United States Patent [19]

Quigley et al.

[11] Patent Number: 4,510,801
[45] Date of Patent: Apr. 16, 1985

[54] CONTROLLED HEATER FOR DRILLING MUD TESTING SYSTEM

[75] Inventors: M. Scott Quigley, Garland; Gordon A. Russell, Dallas, both of Tex.

[73] Assignee: Mobil Oil Corporation, New York, N.Y.

[21] Appl. No.: 518,568

[22] Filed: Jul. 29, 1983

[51] Int. Cl.³ .................................................. G01N 25/00
[52] U.S. Cl. ................................................. 73/153; 374/45
[58] Field of Search ......................... 73/153, 61.4, 64.1, 73/53; 374/45; 219/201, 476

[56] References Cited

U.S. PATENT DOCUMENTS 3,473,368 10/1969 Roper ................................ 73/61.4 X
4,304,122 12/1981 Tentor .............................. 73/153 X Primary Examiner—Jerry W. Myracle
Attorney, Agent, or Firm—Alexander J. McKillop; Michael G. Gilman; Charles J. Speciale

[57] ABSTRACT

Temperature control apparatus for a system for testing drilling mud includes instrumentation for measuring the parameters of the drilling mud, and a pump for pumping the drilling mud in a recirculating path through the instrumentation. A mud heater in the recirculating path heats the mud and a heat exchanger connected in the front of the heater in the recirculating path cools the mud before it is heated. The heater and the heat exchanger are controlled to maintain a constant differential across the heater. The heater is constructed in a manner which provides low thermal mass, thereby providing a fast response time for changes in temperature.

6 Claims, 3 Drawing Figures

CONTROLLED HEATER FOR DRILLING MUD TESTING SYSTEM

BACKGROUND OF THE INVENTION

This invention relates to a controlled heater for a system for testing the parameters of drilling mud and more particularly, to a heater which is quickly and accurately controlled to a desired temperature.

This invention relates to apparatus for periodically flushing drilling mud from a system for testing the parameters of drilling mud, and more particularly, to a flush pump which supplies a volume of pressurized flush water upon demand.

In the drilling of wells, such as oil or gas wells, by the rotary method, a drilling mud is circulated from the surface of the earth to the drill bit and back to the surface again for the purposes of cooling the drill bit, removing earth cuttings from the bore hole, and imposing a hydrostatic pressure on the drilled earth formations to prevent flow of fluid therefrom into the well bore hole. In a drilling mud containing water and clay, the rheological properties of plastic viscosity, gel strength, and yield point, which must be maintained within limits in order that the drilling fluid remain pumpable and perform its desired functions, depend largely upon the concentration of clay solids and the extent to which the clay solids are hydrated by and dispersed within the water contained in the fluid.

Drilling muds are used under a wide variety of conditions which require that different compositions be used. For example, where the well bore hole passes through formations containing clay, the clay admixes with the drilling fluid and this clay is hydrated by and dispersed by the water in the drilling fluid, thereby increasing the concentration of dispersed clay solids. The increase in the concentration of dispersed clay solids deleteriously affects the rheological properties of the drilling fluid. Accordingly, where control of rheological properties, is important, the drilling fluid should have a minimum change in such properties with increasing concentrations of clay solids.

Usually, drilling muds are shear thinning, i.e., they increase in viscosity at low shear rates and decrease in viscosity at high shear rates, whereby the cuttings may be readily separated from the drilling fluid at the surface of the earth and, in the event circulation of drilling fluid is stopped for any reason, the cuttings will be properly suspended by the drilling fluid within the well and not sink to the bottom thereof with resultant danger of sticking drill pipe. The rheological properties of a drilling mud are ordinarily imparted to it by employing a clay such as bentonite as one of the constituents. Since one of the functions of a drilling fluid is to impose a hydrostatic pressure on the formations penetrated by the well, it is desirable that the drilling mud have the correct density, and density of a drilling mud is increased by adding a weighting agent such as barite. Drilling muds also often contain caustic soda which is added to solubilize certain constituents, inhibit fermentation of organic additives, reduce the effect of contaminants picked up during drilling and to effect other results depending on the type of drilling fluid being employed.

Another property desired in a drilling mud is that of resisting gelation at high temperature. With increasing depth of the well, the bottom hole temperature increases. In many wells, these temperatures exceed 300° F. With aqueous drilling fluids, high temperatures induce cementation reactions between clay minerals and various drilling fluid additives. As a result, the drilling mud tends to attain excessively high gel strengths. With gelation, excessively high pump pressures are required to break circulation with the result that often loss of the drilling mud occurs by being forced into permeable formations. Additionally, gelation can prevent logging tools from reaching the bottom of the well.

Frequently, during the drilling of a well, drilling conditions change. Changes in temperature occur. The character of the formations being drilled may change, as, for example, salt may be encountered. Each change in drilling conditions can affect the properties of the drilling mud. Frequently, to counteract the effect of the changed drilling conditions on the properties of the drilling mud a change in the composition or character is required.

The foregoing and other considerations, dictate that drilling muds be tested under conditions which closely approximate conditions which would be encountered during drilling. By adding different additives, and by subjecting the drilling mud to various conditions of temperature and pressure, a determination can be made as to whether the mud will perform adequately under actual drilling conditions.

One of the requirements of such a system is that the temperature of the drilling mud be accurately controlled, and that the mud be quickly brought to the desired temperature. In prior drilling mud testing systems of which we are aware, the thermal response time is very long because the thermal mass of the heater is large. For example, the mud flows across a large piece of steel which has heaters on it. Such a heater can provide accurate temperature control, but the thermal mass is so large that heating, or cooling, the heater to a given temperature takes a long time.

It is an object of the present invention to provide a heater for a drilling mud testing system which has a fast response time and accurate temperature control.

RELATED APPLICATIONS

"FLUSHING APPARATUS FOR A DRILLING MUD TESTING SYSTEM", Seal, Ser. No. 518,336, filed July 29, 1983 now U.S. Pat. No. 4,483,189.

SUMMARY OF THE INVENTION

In accordance with the present invention, the temperature of drilling mud in a testing system is controlled by a system which includes a mud heater and cooling means connected in front of the heater. The mud is cooled to a temperature such that a constant temperature differential is maintained across the heater. Because the temperature differential across the heater is maintained constant, accurate control of mud temperature is obtained.

In accordance with an important aspect of the invention, the mud is heated in an insulated enclosure of low density ceramic material having electrical heaters embedded therein. The mud is heated in a helical tube which extends through the enclosure. The air within the heater is heated by the low density ceramic material and it in turn heats the drilling mud passing through the helical tubes. The watt density is low to prevent baking the mud onto the tube walls. The thermal mass of the heater is very low so the response time is very fast.

SHORT DESCRIPTION OF THE DRAWINGS

DESCRIPTION OF THE PREFERRED EMBODIMENT

Figure 1:
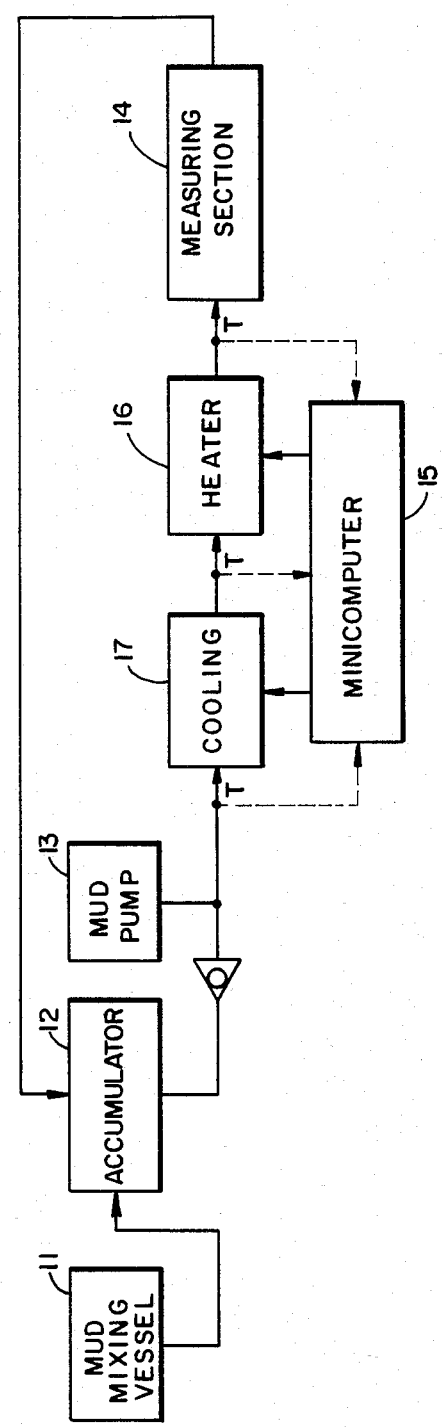
FIG. 1 depicts the drilling mud testing system with the heater of the present invention.

Referring to FIG. 1, the system for testing drilling mud includes a mixing vessel 11 in which mud to be tested is mixed. The mud is pressurized to the desired pressure in accumulator 12. A pump 13 pumps the mud in a recirculating loop through the measuring section 14 under control of a minicomputer 15. A mud heater 16 is connected in the recirculating path. A heat exchanger 17 providing cooling for the recirculating mud is connected in front of the heater in the recirculating path. Minicomputer 15 receive temperature inputs from thermocouples in the recirculating mud path. It controls the heater 16 and the cooling heat exchanger 17 to maintain a constant temperature differential across the heater 16.

The system is arranged to maintain a constant temperature increment across the heater 16. In order to provide rapid heating of the drilling mud initially, a large capacity heater is required. Such a large capacity heater cannot be used to efficiently control the temperature of the drilling mud after it has reached the desired temperature. This requires small changes in temperature when the system is operating, which would require turning heater elements on and off. In order to avoid this, the mud is first cooled in a cooling heat exchanger 17 before it enters the heater. The cooling is relatively small, for example, from approximately 400 F. to 375 F. The heater 16 supplies a constant amount of heat to the slightly cooled mud.

Figure 2:
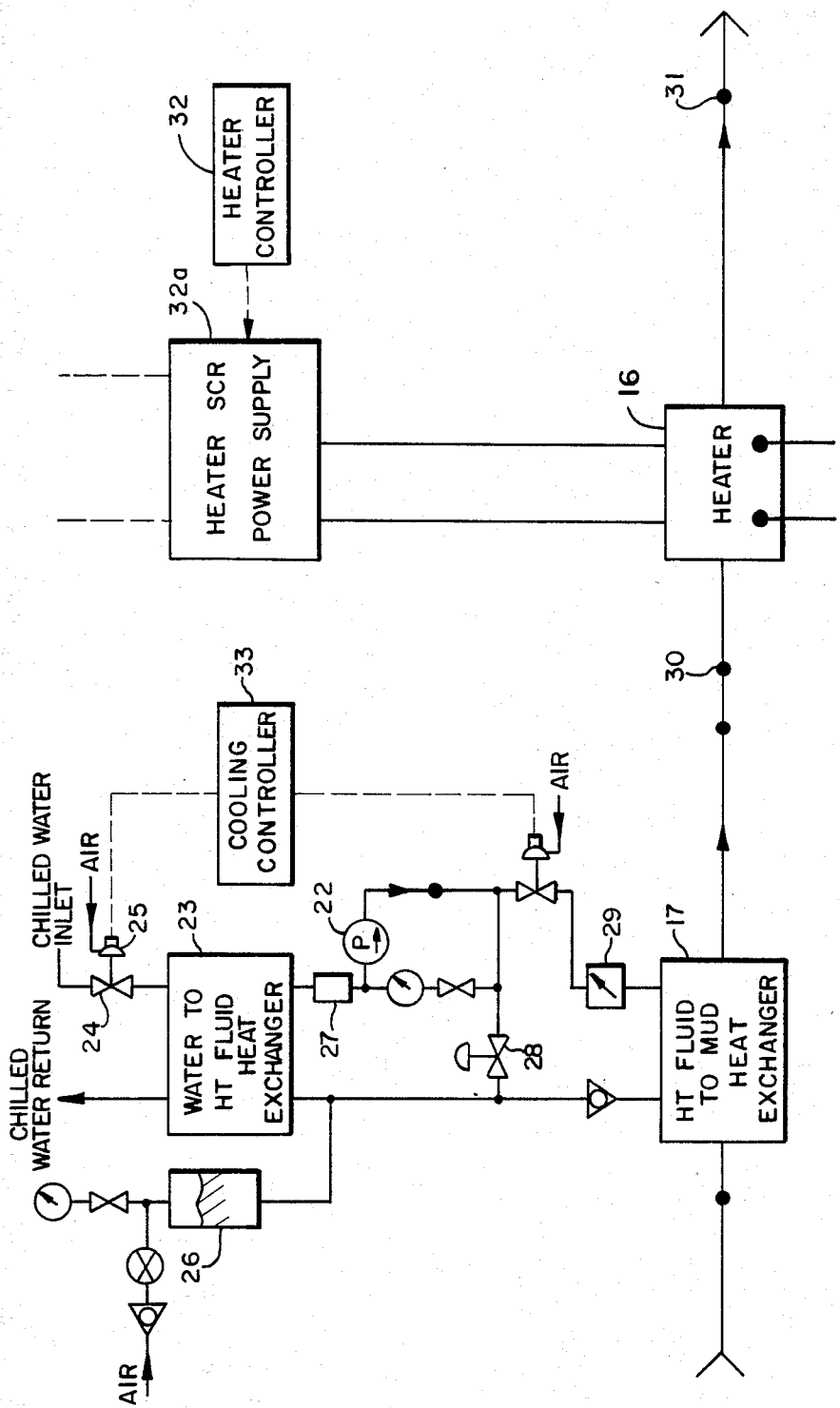
FIG. 2 shows the cooling and heating section in more detail.

FIG. 2 shows the cooling heat exchanger and the heater in more detail.

A heat transfer fluid such as silicon oil, is the heat exchange medium in heat transfer 17. Pump 22 circulates the heat transfer fluid between the heat exchanger 17 and the heat exchanger 23. Chilled water is supplied to heat exchanger 23 through the valve 24. A reservoir 26 contains the heat exchanger fluid.

Flow switch 27 is operated when the system is flowing properly. A back pressure regulator 28 and a flow meter 29 are provided to ensure proper flow of heat exchanger fluid through the heat exchanger 17.

Thermocouples 30 and 31 sense the temperature at the inlet and the outlet of heater 16. The heater controller controls the heater power supply 32a to bring the mud temperature up to its desired level, for example, 400° F.

Figure 3:
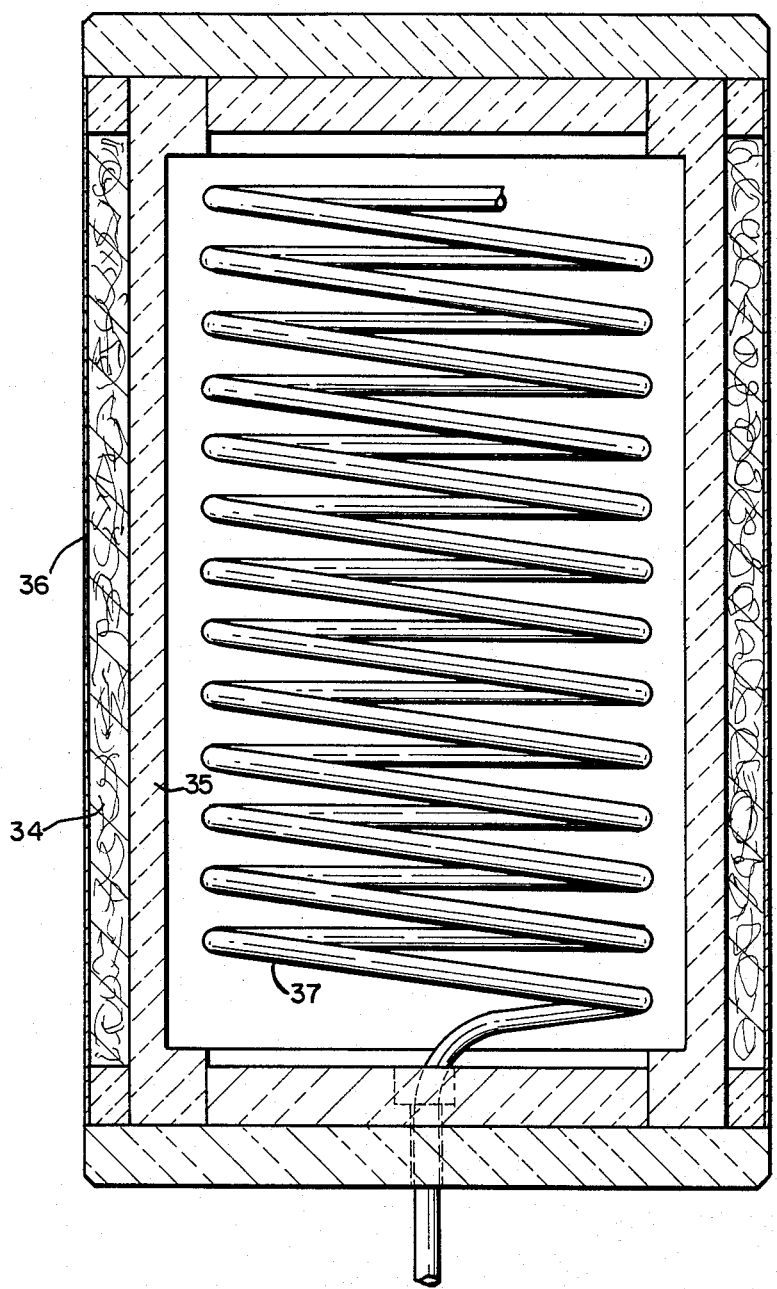
FIG. 3 shows the construction of the heater.

FIG. 3 shows the construction of the heater such that it has a low thermal mass adapted to provide a quick response time for the heater. The enclosure includes an outer wall 34 constructed of ceramic fiber insulation material and an inner wall 35 of ceramic fiber heater material. Commercially available material suitable for the construction of the enclosure is available from Watlow Heater Company, St. Louis, Mo. In a particular embodiment of the invention, the wall 35 was constructed of two halfcircular units to make a 14" inner diameter enclosure which was 24" long, of which 20" was heated. This heater had a heating capacity of 9.6 kw.

A stainless steel jacket 36 completes the enclosure. A double helically coiled tube 37 carries drilling mud through the heater enclosure. Only a single coil is shown, but another coil is installed inside the coil which is shown to provide additional heating capacity. In an exemplary embodiment, the helical tube 37 was a $\frac{5}{8}$" outside diameter by $\frac{1}{2}$" inside diameter 316 stainless steel seamless tubing.

While a particular embodiment of the invention has been shown and described, various modifications of the invention are within the true spirit and scope of the invention. The appended claims are, therefore, intended to cover all such modifications.

What is claimed is:

1. A temperature control apparatus for a system for testing drilling mud comprising:
    means for measuring the parameters of said drilling mud
    means for pumping said drilling mud in a recirculating path through said means for measuring;
    a mud heater in said recirculating path;
    cooling means connected in front of said heater in said recirculating path; and
    means for controlling said heater and said cooling means to maintain a constant temperature differential across said heater.

2. The temperature control apparatus recited in claim 1 wherein said mud heater comprises:
    an enclosure;
    heating elements in said enclosure; and
    a coiled tube carrying mud through said enclosure, said heater having low thermal mass with a fast response time for changes in temperature.

3. The temperature control apparatus recited in claim 2 wherein said tube is formed in a helix.

4. The temperature control apparatus recited in claim 3 wherein said tube is formed in a double helix.

5. The temperature control apparatus recited in claim 2 wherein said enclosure includes a low-density ceramic fiber insulation.

6. The temperature control apparatus recited in claim 2 wherein said enclosure includes ceramic fiber heater material.

* * * * *